United States Patent
Ternes et al.

(10) Patent No.: US 9,750,938 B2
(45) Date of Patent: Sep. 5, 2017

(54) VISUALIZATION OF BIOLOGICAL ENVIRONMENT IMPACT ON IMPLANTED THERAPY

(71) Applicant: Cardiac Pacemakers, Inc., St. Paul, MN (US)

(72) Inventors: David J. Ternes, Roseville, MN (US); Brian D. Soltis, St. Paul, MN (US); LeAnne M. Eberle, Mahtomedi, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/630,211

(22) Filed: Feb. 24, 2015

(65) Prior Publication Data
US 2015/0258341 A1 Sep. 17, 2015

Related U.S. Application Data

(60) Provisional application No. 61/951,079, filed on Mar. 11, 2014.

(51) Int. Cl.
| *A61N 1/00* | (2006.01) |
| *A61N 1/36* | (2006.01) |
| *A61N 1/372* | (2006.01) |
| *A61N 1/365* | (2006.01) |
| *A61N 1/378* | (2006.01) |
| *A61N 1/08* | (2006.01) |

(52) U.S. Cl.
CPC ..... *A61N 1/36142* (2013.01); *A61N 1/37247* (2013.01); *A61N 1/365* (2013.01); *A61N 1/36135* (2013.01); *A61N 1/378* (2013.01); *A61N 2001/083* (2013.01)

(58) Field of Classification Search
USPC .......................................................... 607/17
See application file for complete search history.

(56) References Cited

U.S. PATENT DOCUMENTS

| 2010/0114224 A1* | 5/2010 | Krause | ............... A61N 1/36521 607/8 |
| 2011/0040547 A1* | 2/2011 | Gerber | ............... A61N 1/36185 703/11 |

\* cited by examiner

*Primary Examiner* — Nicole F Johnson
*Assistant Examiner* — Nicole F. Lavert
(74) *Attorney, Agent, or Firm* — Schwegman Lundberg & Woessner, P.A.

(57) ABSTRACT

An implantable medical device (IMD) system communicates to a user information regarding the surrounding biological environment and the influence of that surrounding biological environment on IMD functionality. This influence can be static or dynamic. Providing information on the biological environment can assist the user in determining therapy parameters for an individual patient with an IMD.

15 Claims, 16 Drawing Sheets

VISUALIZATION OF BIOLOGICAL ENVIRONMENT IMPACT ON IMPLANTED THERAPY

CLAIM OF PRIORITY

This application claims the benefit of under 35 U.S.C. §119(e) of U.S. Provisional Patent Application Ser. No. 61/951,079, filed on Mar. 11, 2014, which is herein incorporated by reference in its entirety.

TECHNICAL FIELD

The document relates generally to implanted therapy and more particularly to visualization of biological environment impact on implanted therapy.

BACKGROUND

An implantable medical device (IMD) may deliver electrical stimulation using a transmission of a pulsed electrical signal to a desired biological target, such as a cardiac or neurological target. The extent and effectiveness of stimulation depends upon various properties of the pulsed electrical signal, such as pulse amplitude, frequency, pulse width, duty cycle, and the like. The IMD is programmed with a number of stimulation parameters corresponding to the properties of the pulsed electrical signal. The stimulation parameters are programmed into the IMD by a user, such as a physician, patient, patient assistant, robot or a medical professional, using an external programming device. The biological environment of the IMD, leads and electrodes may affect the ability of the IMD to provide the programmed therapy. For example, system output may not match expected output for certain combinations of stimulation parameter values (such as amplitude) and the electrical load experienced in the biological environment.

Generally, limitations of an IMD system and related information are mentioned in a manual accompanying the IMD. However, the user does not have access to or time to check the manual for the unique limitations of a particular biological environment, thereby delaying or preventing appropriate selection of parameters for implanted therapy. Therefore, there is a need for implanted therapy systems that can communicate the biological environment limitations of parameter selection to the user, when the user is programming the system.

SUMMARY

An implanted therapy system communicates the biological environment impact on therapy to a user. In various embodiments, limitations of electrical stimulation parameter selection may be identified and may be displayed using a parameter selection window on an interface of an external device, such as an interface for programming the implanted therapy system.

According to various embodiments, a method for communicating biological environment impact on therapy may include measuring a parameter associated with a biological environment for a system including an implantable medical device (IMD) configured for delivering electrical stimulation therapy. A limit of the therapy that can be delivered by the IMD may be determined based on the measured parameter. The limit may be displayed to a user using an interface of an external device, the external device configured to communicate with the IMD. Examples of electrical stimulation therapy include, but are not limited to, neurostimulation therapy, cardiac rhythm management (CRM) therapy and deep brain stimulation therapy.

In various embodiments, measuring a parameter associated with a biological environment includes sensing impedance for at least a portion of a lead system connected to the IMD. An example of the method includes determining voltage compliance based on the sensed impedance and calculating a limit of electric current level that can be delivered by the IMD based on the determined voltage compliance. The limit may be displayed on the interface.

Another example of the method includes determining charge density based on the sensed impedance, determining potential for nerve damage from therapy delivery by the IMD based on the determined charge density, and displaying the determined potential for nerve damage using the interface.

Another example of the method includes determining charge used over time based on the sensed impedance and settings input by the user, measuring battery capacity for the IMD, calculating device longevity for the IMD based on the determined charge and battery capacity, and displaying the device longevity to a user using an interface of an external device.

In various embodiments, the present subject matter provides a method for measuring a parameter associated with a biological environment for a system including an implantable medical device (IMD) configured for delivering electrical stimulation therapy. An example of the method includes sensing a parameter related to intrinsic cardiac function (such as AV delay or heart rate, for example) for a patient. A combination of input parameters for a therapy may be determined that increase a likelihood of undesired amounts of cardiac pacing for the patient based in part on the sensed parameter. The combination of input parameters may be displayed to a user using an interface of an external device.

According to various embodiments, a system for communicating biological environment impact on therapy may include at least one stimulation lead having at least one electrode, the lead configured to place the at least one electrode proximate to a therapy delivery target. The system may include an implantable medical device (IMD) coupled to at least a portion of the at least one lead. The IMD may include a stimulator adapted to deliver an electrical signal through the at least one electrode to stimulate the target to provide therapy, and a controller. The controller may be programmed with the therapy and programmed to measure a parameter associated with a biological environment for one or more of the at least one stimulation lead and the IMD. The system may also include an external device configured to communicate with the IMD. The external device may include a processor and an interface configured to display a determined limit of the therapy that can be delivered by the IMD based on the measured parameter.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9B-9C illustrate examples of a color palette display such as may be displayed on the programmer of FIG. 3;

FIGS. 13B-13C illustrate embodiments of an interactive window 1382 and a color palette 1384 for display on the programmer of FIG. 3 to allow a user to select a stimulation parameter to promote RV pacing.

DETAILED DESCRIPTION

Figure 1:
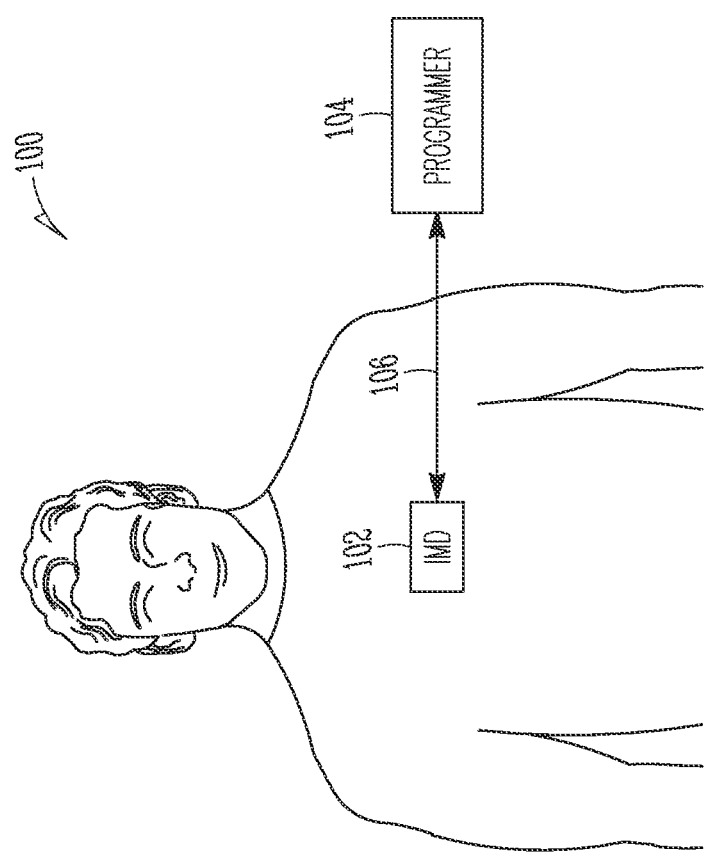
FIG. 1 illustrates an example of an implanted therapy system that includes a programmer.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The term "compliance voltage" refers to the maximum voltage at which a current source can supply a constant current to a load resistance. The compliance voltage range is the range of voltages over which the current source can maintain a constant current. Corresponding to the compliance voltage range, there is a compliance range of load resistances for which the current source remains voltage compliant. The term "charge density" refers to the measure of electric charge per unit area of the surface of an electrode of an implanted stimulation system.

The term "longevity" refers to time duration for which a power source can deliver energy to an implantable medical device (IMD) or the time duration for which an IMD can continue to deliver programmed therapy with present battery capacity.

The term "Right Ventricle (RV) only pacing" refers to stimulation of only the right ventricle of a patient's heart. The term "Left Ventricular (LV) only pacing" refers to stimulation of only the left ventricle of a patient's heart. The term "Bi-Ventricular (BiV) pacing" or "Cardiac Resynchronization Therapy (CRT)" refers to stimulation of both ventricles of a patient's heart. A "user" may include a physician, patient, caregiver or other healthcare provider that use the disclosed systems and methods for treating a patient.

Various embodiments of the present subject matter provide an IMD system that communicates to a user information regarding the surrounding biological environment and the influence of that surrounding biological environment on the IMD's functionality. This influence can be static or dynamic, in various embodiments. Providing information on the biological environment can assist the user in determining the therapy parameters best suited for an individual patient with an IMD.

An example of a surrounding biological environment is the encapsulation and healing that occurs around the electrodes of an implanted lead. These influences affect the impedance into which the IMD must deliver therapy. Voltage compliance, which is dependent on the impedance load, may limit the ability of an IMD to deliver programmed current amplitudes. In addition, charge delivered for a programmed voltage amplitude is impacted by the impedance. Predicted power consumption is dependent on many factors including the impedance of the surrounding biological environment. Also, maximum allowable programmed frequency of pulse delivery may be limited by the impedance load and time duration of recharge. Using a graphical display to illustrate how a combination of a programmable parameter and this facet of the surrounding biological environment impacts IMD functionality can help guide the user in programming.

Another example of a surrounding biological environment is intrinsic cardiac activation. The likelihood of RV or CRT pacing that can occur is a combination of a programmable parameter and an aspect of intrinsic cardiac activity. For instance, setting the programmed lower rate limit for pacing of a cardiac rhythm management device below the intrinsic resting heart rate will result in reduced RV pacing. In another example, setting the programmed sensed AV delay of a cardiac rhythm management device to be shorter than the intrinsic AV delay will result in increased CRT pacing. As discussed above, illustrating how the combination of a programmable parameter and this facet of the surrounding biological environment impacts IMD functionality can help guide the user in programming.

These examples are not intended to be an exclusive or exhaustive list. Other aspects of the surrounding biological environment, such as intrinsic nerve activity, measures of chronotropic incompetence or measures of blood pressure, may also influence how various IMDs function. These and other aspects or facets of the surrounding biological environment can be used to guide the user in programming the IMD without departing from the scope of the present subject matter.

The disclosed systems and methods generally apply to any IMD system. Examples of IMD systems include neurostimulation therapy systems and cardiac therapy systems. An example of a cardiac therapy system is a cardiac rhythm management (CRM) system. An example of a neurostimulation therapy is autonomic modulation therapy (AMT), and an example of AMT is a vagal stimulation therapy (VST). The present subject matter can be used for other types of cardiac therapy systems, neurostimulation therapy systems, or other implantable or implanted therapy systems, without departing from the scope of the present subject matter.

AMT, such as VST, has been applied to modulate various physiologic functions and treat various diseases. For example, cardiovascular functions are modulated by neural signals in portions of the autonomic nervous system. The neural activities in the nerves innervating the heart are known to regulate, among other things, heart rate, blood pressure, and myocardial contractility. Modulation of such neural activities by neurostimulation therefore provides for modulation of such cardiovascular functions. For example, electrical stimulation applied to the vagus nerve is known to decrease the heart rate and the contractility, lengthening the systolic phase of a cardiac cycle, and shortening the diastolic phase of the cardiac cycle. In addition, vagus nerve stimulation is also known to be effective in treating disorders including, but not limited to, depression, anorexia nervosa/ eating disorders, pancreatic function, epilepsy, hypertension, inflammatory disease, and diabetes.

Various embodiments disclosed herein provide systems and methods for communicating biological environment limitations for selecting values of one or more parameters in an IMD that may include one or more of a cardiac rhythm management system, a neurostimulation system, or a combination of systems. Some of the disclosed embodiments enable communication of such limitations to a user. This communication may improve therapy for the patient, and/or may improve battery longevity fir the IMD.

FIG. 1 illustrates an example of an implanted stimulation system 100. The system may include an implantable medical device (IMD) 102 implanted into a patient's tissue and an external device such as a programmer 104 external to the patient's body. The programmer 104 and the Imp 102 may communicate via a telemetry link 106. In various embodiments, the IMD 102 may integrate a cardiac rhythm management (CRM) system (not shown) for modulating cardiovascular functions with neural sensing and stimulation devices. The CRM system may sense cardiac electrical activities for delivering cardiac stimulations. Some examples of the CRM systems are pacemakers, cardioverter/ defibrillators, combined pacemaker-cardioverter/defibrillators, and cardiac resynchronization therapy (CRT) devices.

In various embodiments, the system 100 senses neural activities to indicate a need for cardiac stimulation and/or to control the timing of pacing pulse deliveries. In addition, the system 100 senses cardiac activities to control the timing of neural stimulation pulse deliveries, such as to synchronize neural stimulation to cardiac cycles. Embodiments of the system without sensing are included within the scope of the present subject matter.

Figure 2:
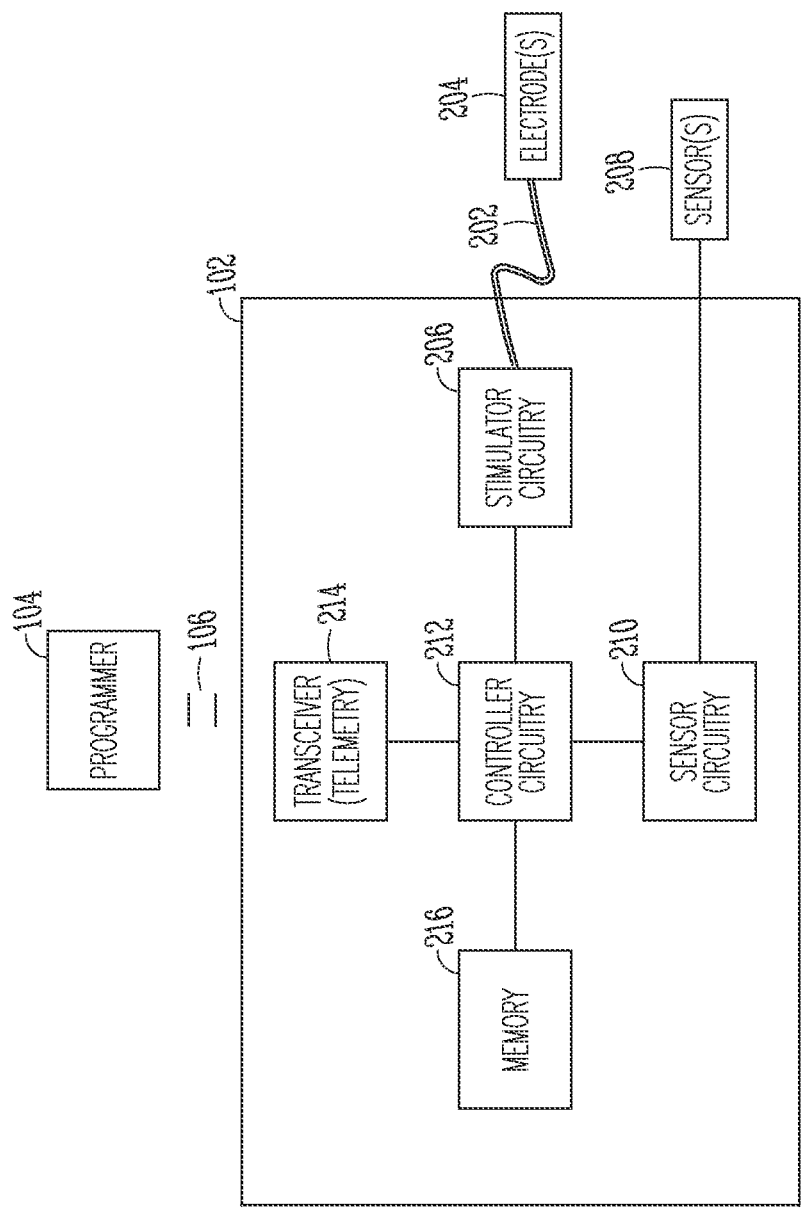
FIG. 2 illustrates an example of a system that includes an implantable medical device (IMD) and an external device such as the programmer of FIG. 1.

FIG. 2 illustrates an example of a system that includes an implantable medical device (IMD) and an external device such as the programmer 104 of FIG. 1. The IMD 102 may be coupled to at least a portion of a stimulation lead 202 having one or more electrodes 204 disposed on the lead 202. In various embodiments, the lead 202 may include cuff electrode(s), helical electrode(s), or other electrode configuration configured to deliver monopolar, bipolar or multipolar stimulation. The lead 202 may have dimensions suitable to place the one or more electrodes 204 proximate to a site of a neural pathway. For example, the electrode(s) may be intravascular electrodes or may be configured to otherwise be placed proximate to the nerve. For example, electrode(s) may be placed in the internal jugular vein (IJV) to stimulate a cervical vagus nerve, or may be placed in the carotid sheath at a site proximate the vagus nerve of a patient. Monopolar delivery occurs when a selected electrode is activated along with a reference electrode amongst the electrodes 204, so that electrical energy is transmitted between the selected electrode and the reference electrode. Monopolar delivery may also occur when one or more of the selected electrodes are activated along with a large group of electrodes located from the electrode(s) 204 so as to create a monopolar effect; that is, electrical energy is conveyed from the selected electrode(s) 204 in a relatively isotropic manner. Bipolar delivery occurs when two of the electrodes 204 are activated as anode and cathode, so that electrical energy is transmitted between the activated electrodes. Multipolar delivery occurs when multiple electrodes 204 are activated.

The IMD 102 may include a stimulation circuitry 206, sensor circuitry 210, a controller circuitry 212, a transceiver/ telemetry circuitry 214, and a memory 216. The stimulation circuitry 206 is electrically coupled to the electrodes 204 using conductors of the stimulation lead 202. The stimulation circuitry 206 delivers electrical signals to the electrodes 204 to stimulate the desired target to provide stimulation. The programmer 104 may be used to program stimulation parameters into the memory 216. The controller circuitry 212 may use the programmed stimulation parameter to control the stimulator circuitry 206 to generate the stimulation that corresponds to the programmed stimulation parameters.

The IMD 102 may include one or more sensor(s) 208 for sensing physiological parameters such as cardiac contractions which may be used to determine heart rate (beats per minute or bpm) or rhythm information, tissue impedance (ohms), intrinsic atrial-ventricular (AV) delay (seconds), heart sounds, respiratory sounds, pressure, respiration, acceleration (activity and posture), nerve traffic, chemical parameters, or the like. The sensor(s) 208 can be located external to the IMD 102 housing, or encapsulated within the IMD 102 housing. The sensor(s) 208 can be attached to the sensor circuitry 210. The sensor circuitry 210 can include various components, such as instrumentation amplifiers, signal filters, etc., that process the electrical signals for determining the physiological parameters.

The sensor circuitry 210 feeds the physiological parameters to the controller circuitry 212. The controller circuitry 212 controls various operations of the IMD 102 and can include programmable microprocessors, microcontrollers, or the like. For example, the controller circuitry 212 may be programmed to perform therapy and send control signals to the neural stimulator circuitry 206 for transmitting electrical stimulation pulses to the electrodes 204. The controller circuitry 212 analyzes the determined physiological parameters and other parameters inputted by the user using the programmer 104 to assess appropriate therapy regime and send control signals to neural stimulation circuitry 206 for transmitting stimulation pulses to the patient's target tissue.

The transceiver/telemetry circuitry 214 may communicate the determined physiological parameters to the programmer 104 located external to the patient's body. The telemetry circuitry 214 may use a suitable communication protocol, such as, the medical implant communication service (MICS) in the bandwidth of 402-405 MHz, for communicating with the programmer 104.

The memory 216 is configured for storing the stimulation parameters received from programmer 104 and the physiological parameters determined by the sensory circuitry 210. For example, the memory 216 can store at least one year of daily lead impedance measurements and/or program usage. In another example, the memory can store lifetime energy use data for the device. In yet another example, the memory may store a list of measurements over time of a sensed parameter, for example, heart rate, for assessing the appropriate therapy regime.

The IMD 102 can be encased in a biocompatible metallic, polymeric, or composite housing (not shown), according to various embodiments. The housing protects the components of the IMD 102 from coming in contact with the patient's tissue. Additionally, the IMD 102 includes a power source such as a battery for delivering power to the IMD 102.

Figure 3:
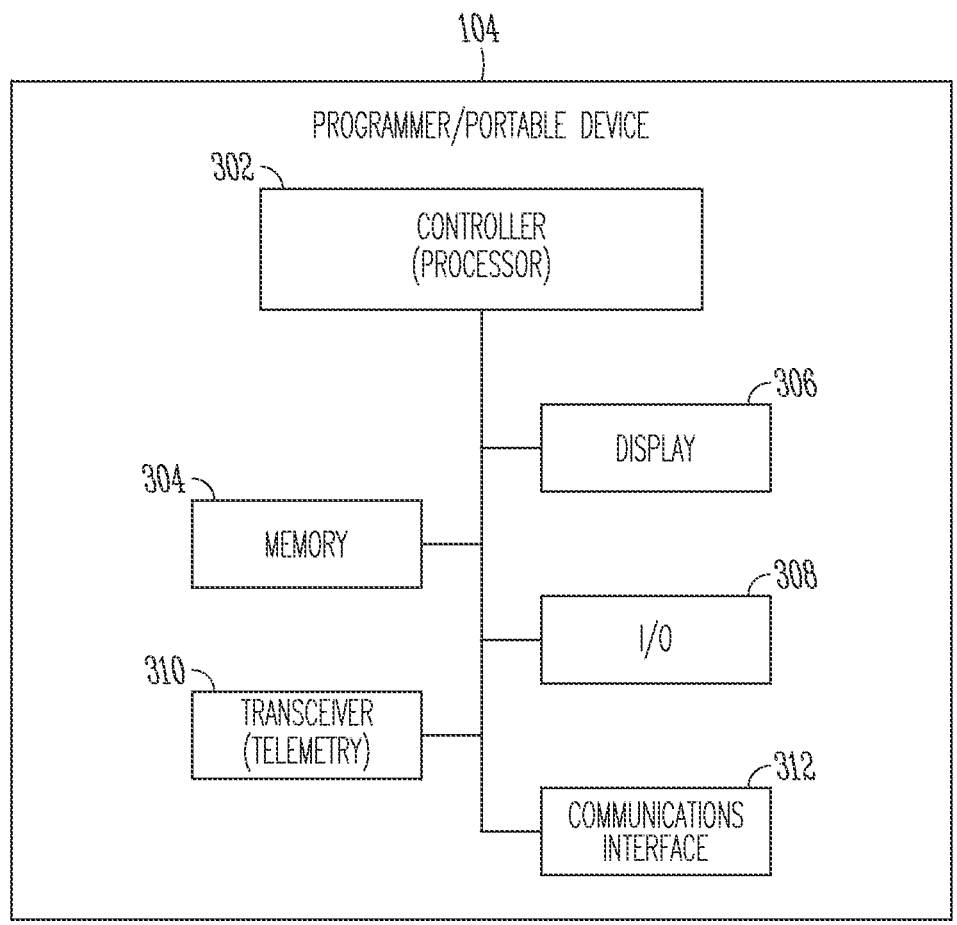
FIG. 3 illustrates an example of an external device such as the programmer of FIG. 1.

FIG. 3 illustrates an example of an external device such as the programmer 104 of FIG. 1. The programmer 104 may be a portable device or hand held device that includes a controller/processor 302, a memory 304, a display 306, an input/output (I/O) unit 308, a transceiver/telemetry unit 310, and a communications interface 312. The programmer 104 may be housed within a polymeric, metallic or composite housing.

The controller 302 controls various operations of the programmer 104. The controller 302 may include any suitable computing device, for example, microprocessors, microcomputers, microcontrollers, digital signal processors, central processing units, state machines, logic circuitries, and/or any devices that manipulate signals based on operational instructions. Among other capabilities, the controller 302 may be configured to fetch and execute computer-readable instructions stored in the memory 304. Further, the controller 302 may be configured with standard or customized operating systems, such as, Microsoft Windows, Linux, Unix, or the like, with one or more custom software installed to control the operations of other components of the programmer 104. The controller 302 may be a fixed or portable computing device such as a desktop computer or a laptop.

The display 306 can be any suitable known, related art, or later developed, devices capable of displaying multimedia information. Examples of such displays include, but not limited to, a Liquid Crystal Display (LCD), Light Emitting Diode (LED), and Cathode Ray Tube (CRT) display.

In one embodiment, the controller 302 may generate one or more interactive windows on the display 306, discussed later in greater detail, with desired information in an interactive format for controlling the programmer 104. The interactive windows may allow the user to program and monitor stimulation parameters for controlling the IMD 102. Further, the controller 302 displays limitations of the stimulation parameters to the user, and requests the user to input appropriate parameter values through the I/O unit 308.

The I/O unit 308 allows the user to control and operate the programmer 104 and enter stimulation parameter values to the programmer 104. In some instances, the I/O unit 308 may include input devices, such as keypads, scrolls, mouse, touch screens, or like. The parameter values inputted from the I/O unit 308 are processed in the controller 302 and stored in the memory 304.

The telemetry unit 310 communicates with the IMD 102 using the telemetry link 106 (FIG. 1). In some embodiments, the telemetry unit 310 allows the programmer 104 to control and program the IMD 102. In addition, the telemetry unit 310 allows the programmer 104 to communicate with the IMD 102 (shown in FIG. 2).

In various embodiments, the physiological parameters received by the telemetry unit 310 and the stimulation parameter values input by the user from the I/O unit 308 are processed in the controller 302 to calculate the effects of various parameter values set by the user, discussed in detail later. The effects of some stimulation parameter values selected by the user act as limitations of parameter selection, which are then communicated to the user via multiple techniques, such as, displaying the limitations of parameter values that can be selected on the display 306, using an audio tone/message, or a vibration alert to indicate the limitations.

The communications interface 312 may include a variety of software interfaces, for example, application programming interface, hardware interfaces, for example cable connectors, or both. The communication interface 312 establishing a communication link with an external computing device, such as a laptop or desktop computer for further analysis of the stimulation parameters.

In some embodiment, the controller 302 displays one or more interactive windows on the display 306 for programming the IMD 102, with desired information in an interactive format for controlling the programmer 104. The interactive windows may allow the user to program and monitor stimulation parameters, such as neurostimulation parameters and/or CRM parameters, for controlling the IMD 102. Further, in some embodiments, the controller 302 displays limitations of the stimulation parameters to the user, and requests the user to input appropriate parameter values through the I/O unit 308. These interactive windows may include a parameter selection window for use to select parameters to be used in programming the IMD 102.

Figure 4:
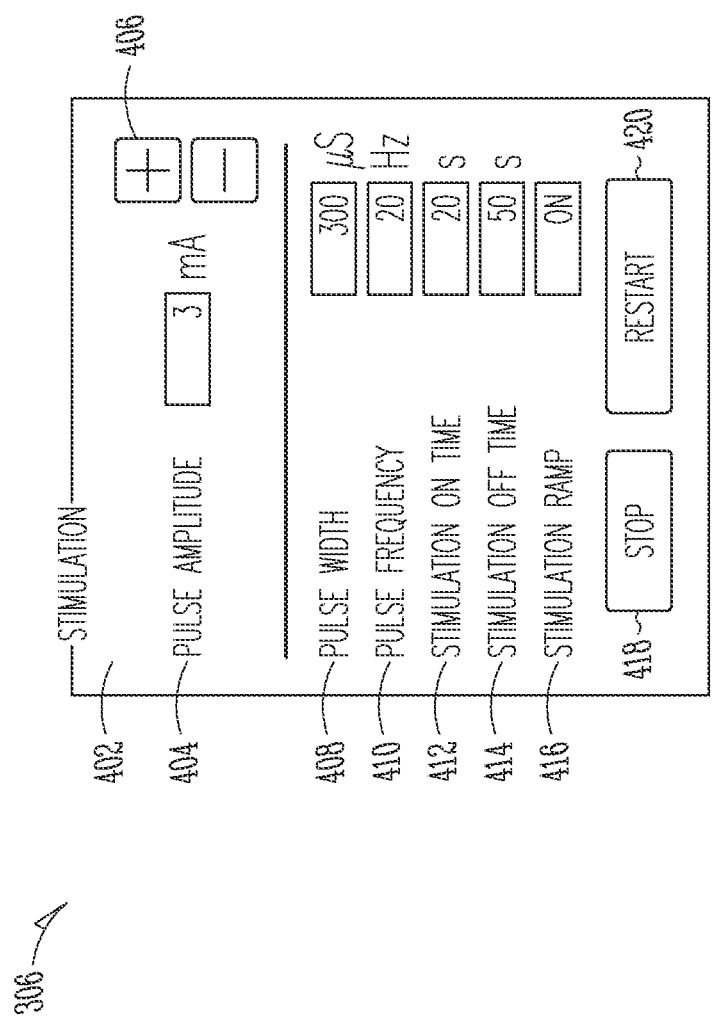
FIG. 4 illustrates an example of a parameter selection window, such as may be used to program the IMD of FIG. 1.

FIG. 4 illustrates an example of a parameter selection window 402 such as may be used to program the IMD 102 of FIG. 2. The window 402 includes one or more parameter fields where the user may select stimulation parameters. By way of example and not limitations, the fields may include a pulse amplitude field 404, a pulse width field 408, a pulse frequency field 410, stimulation ON time field 412, stimulation off time field 414, a stimulation ramp field 416, or various combinations thereof. In addition, the window 402 may include sections for setting other stimulation parameters. The window 402 may include buttons for changing parameter values such as buttons 406 to increase or decrease the value. The window 402 may include buttons for stopping or restarting the stimulation, such as a stop button 418, and a restart button 420. The buttons 406, 418, and 420 may be accessed using one or more input devices in the I/O unit 308, for example, a touch screen or a pointing device such as a mouse, or the like. The controller 302 may use other windows other than window 402 to allow the user to operate and program the stimulation system 100.

The sections below describe various embodiments of methods for measuring physiological parameters, determining limitations of setting one or more stimulation parameter values, and displaying the limitations to the user using the system components discussed above with FIGS. 1-3. In some embodiments, the stimulation system 100 may be configured to perform one or more methods discussed below. Such system configurations include programming the IMD 102 and the programmer 104 to perform the one or more methods.

In some instances, the parameter values selected by the user may not provide the desired stimulation of the patient's body because of the limitations the biological environment places on the capabilities of the MID 102. For example, in a typical IMD, a constant current source delivers stimulation to patient's tissue. In an environment such as human tissue, where the load impedance varies from patient to patient and over time, the constant current source is generally used for stimulation applications. The constant current source provides a predefined or preselected constant current to the tissue if the load is in the compliance range of load resistance. If the load resistance is not in the compliance range of load resistance, the constant current source is not voltage compliant and does not deliver the desired or predefined constant current to the patient. In addition, the current source stops acting as a constant current source and delivers the maximum current amplitude that can be delivered at that load irrespective of the current amplitude selected by the user in a parameter settings.

The programmer 104 may perform a method, by way of example and not limitation, for communicating the limitations of the current source in the IMD 102. The stimulation system 100 may be configured to sense impedance of the patient's tissue, determine voltage compliance of the IMD 102, and calculate the range of electric current level that can be delivered to the patient.

The IMD 102 may have one or more sensor(s) 208 to sense impedance of the patient's tissue for at least a portion of the lead 202. For example, at least two electrodes 204 in the lead 202 can be attached to the sensor circuitry 210. The sensor circuitry 210 may include complex impedance measurement circuits or chips configured to sense tissue impedance using the electrodes 204. The controller circuitry 212 may communicate the sensed impedance to the programmer 104 using the telemetry link 106.

The programmer 104 may receive and store the measured impedance communicated by the IMD 102 in the memory 304, and may use the sensed impedance to determine the voltage compliance of the IMD 102. The controller 302 may calculate a limit of electric current level that can be delivered by the IMD 102 based on the determined voltage compliance, and may communicate the sensed impedance, the determined voltage compliance, and the calculated limit of electric current level to the user by a visual stimulus, an audio tone/message, a vibration alert or the like or combinations thereof.

In some embodiments, the controller 302 may display a visual representation of the measured impedance, the voltage compliance, and the limit of electric current level on the display 306 to communicate with the user. The user can make an informed decision about the limitation of the IMD 102 using the displayed information, while selecting stimulation parameters, such as current amplitude, on the programmer 104.

The controller 302 may display the measured impedance, the voltage compliance, and the limit of electric current level by a number of methods. For example, a color code may be assigned to the calculated current limit. As a more specific example, the current amplitude values below the calculated limit of electric current level in a current amplitude selection window on the display 306 may be colored with a color, such as green, indicating that these current amplitude values do not limit the current supply of the IMD 102; and current amplitude values above the calculated limit of electric current level may be colored with a different color, such as red, indicating that these current amplitude values limit the current supply of the IMD 102. A color palette may be displayed along with selections for programming current level for delivering a therapy.

Figure 5:
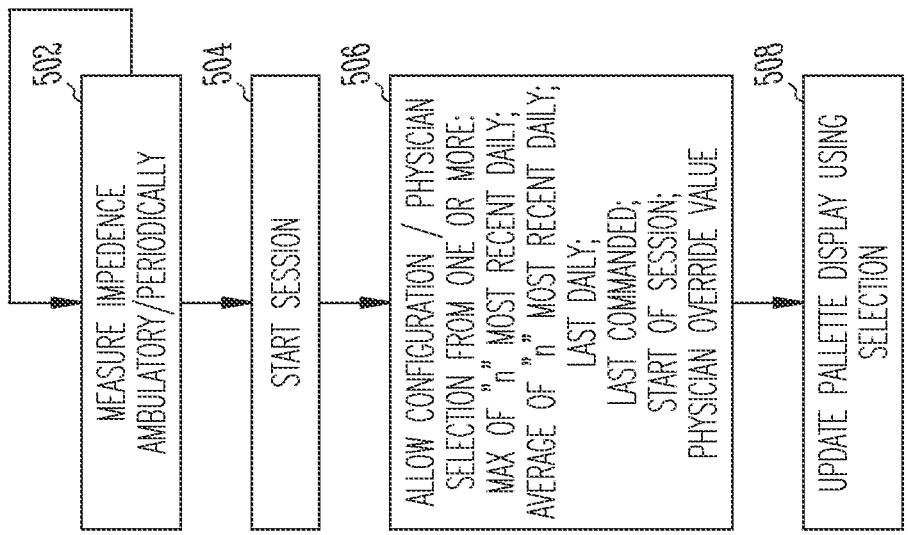
FIG. 5 illustrates an example of a method for communicating a parameter limitation using a patient's measured tissue impedance.

FIG. 5 illustrates an example of a method for communicating a patient's tissue impedance to a user. At 502, the IMD 102 may sense a patient's tissue impedance intermittently (e.g. periodically at defined periods of time) according to a programmed schedule or according to triggering events such as in response to a device request or a user request. As discussed above, the IMD 102 may include one or more sensor(s) 208 to measure tissue impedance. In addition, the IMD 102 can store the periodically measured tissue impedance in the memory 216 and can communicate the tissue impedance data to the programmer 104 when the programmer 104 communicates with the MID 102.

At 504 a programming session may be started. A user may switch on the programmer 104 to start a new programming session. The programmer 104 upon startup may form the telemetry link 106 with the IMD 102 to communicate with the IMD 102 and receive the impedance measurements made by the IMD 102.

At 506, after startup of the programmer 104, the user may use the programmer 104 to display the impedances measured by the IMD 102. The user may select one of many configurations of impedance measurements, or the system may default to one of the configurations. For example, impedance measured at start of session, impedance from last commanded session, impedance measured at the last of every day, average impedance of every week, maximum impedance of every week, impedance measured each time a palette is displayed, impedance input or override by the user, and the like.

At 508, as discussed above, a color palette may be displayed along with selections for programming current level for delivering therapy. The color palette on the display 306 may be updated in real time as impedance measurements are displayed.

Figure 6:
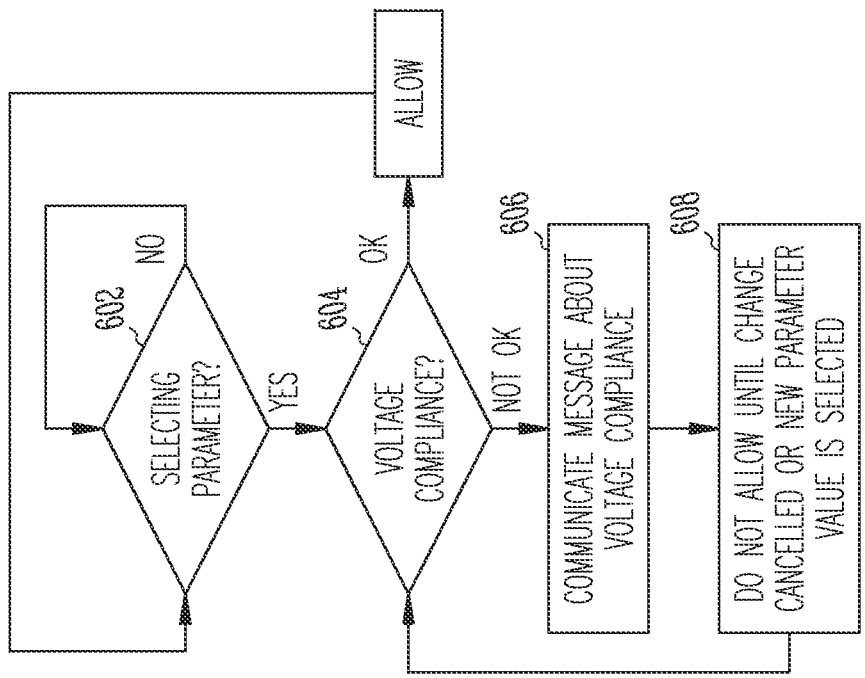
FIG. 6 illustrates an example of a method for communicating the compliance voltage of an IMD, while a user selects a stimulation parameter on the programmer of FIG. 3.

FIG. 6 illustrates an example of a method for communicating the compliance voltage of an IMD 102, while a user selects a neurostimulation parameter. While the depicted embodiment relates to neurostimulation, other types of implantable stimulation systems can be used without departing from the scope of the present subject matter. At 602, the programmer 104 checks if the user selects neurostimulation parameter (e.g. the current amplitude). The programmer 104 waits for the user to select a neurostimulation parameter. The process may continue to 604 when the parameter is selected. At 604, the programmer 104 may determine the voltage compliance of the IMD 102 using the patient's tissue impedance and the selected neurostimulation parameter. In various embodiments, the tissue impedance value is calculated using a method such as in 506. Other methods of calculating tissue impedance value can be used without departing from the scope of the present subject matter. If it is determined that the IMD 102 is voltage compliant, then the controller 302 allows programming of the parameter value selected by the user. At 606, if the IMD 102 is not voltage compliant, then the controller 302 communicates a message about voltage compliance of the IMD 102 to the user. The controller 302 may communicate the message using a window on the display 306. At 608, in addition to communicating a message about voltage compliance, the programmer 104 may allow, may not allow, or may allow only after user confirmation, the programming of the IMD 102. Further, when the user changes the value of the neurostimulation parameter, the programmer 104 checks for voltage compliance again.

Figure 7A:
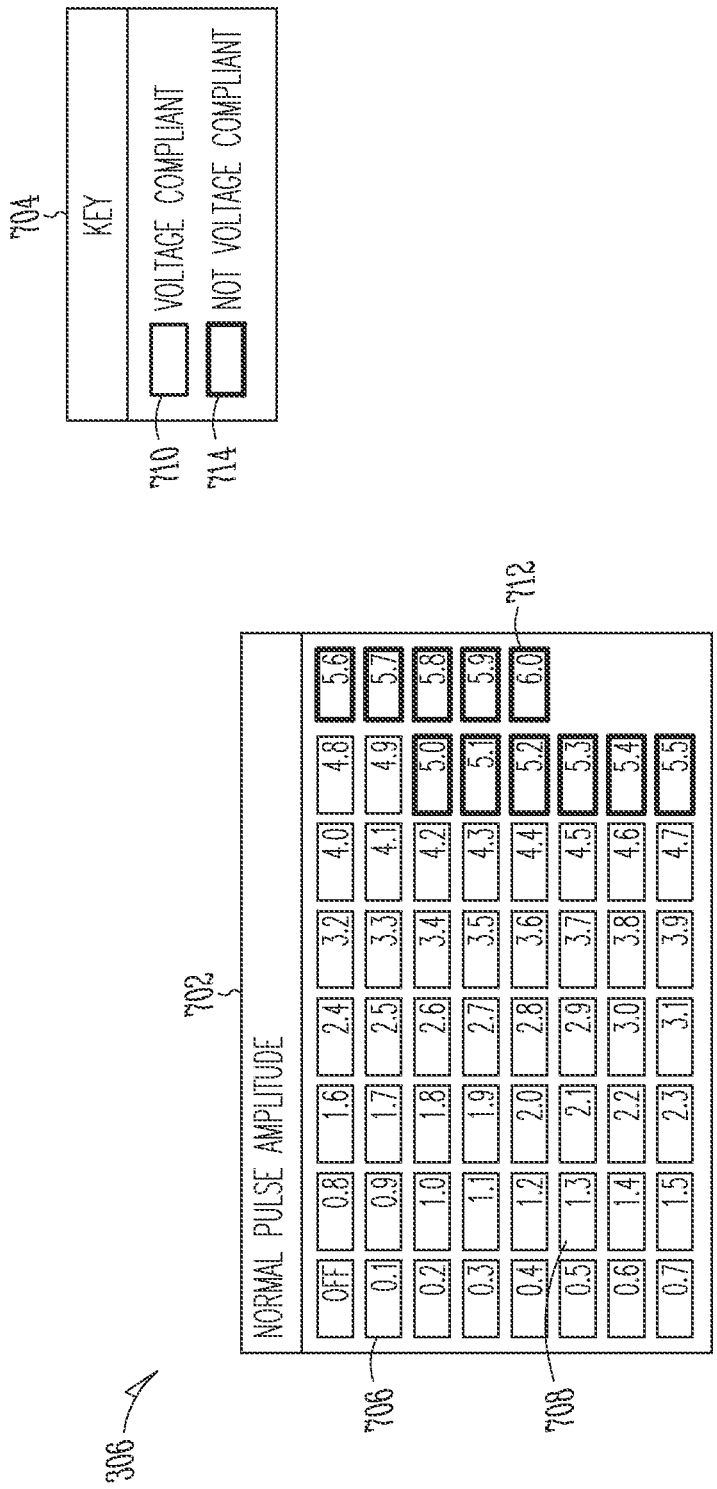
FIG. 7A illustrates, by way of example and not limitation, an embodiment of an interactive window 702 and a color palette 704 for display on the programmer of FIG. 3 to allow a user to select a stimulation parameter.

FIG. 7A illustrates, by way of example and not limitation, an embodiment of an interactive window 702 and a color palette 704 on the display 306 to allow a user to select a neurostimulation parameter (e.g. the current amplitude of the neurostimulation pulses). The interactive window 702 may include a number of buttons 706 for selection of current amplitudes for the neurostimulation. The buttons 706 may be accessed using one or more input devices in the I/O unit 308 such as, for example, a touch screen or a pointing device such as a mouse, or the like. The programmer 104 may highlight the current amplitudes for which the IMD 102 is voltage compliant with a first color highlighting 708 (e.g. green, blue, grey, or the like). The color palette 704 may also include a corresponding description 710 of the color highlighting 708. The programmer 104 may highlight the current amplitudes for which the MD 102 is not voltage compliant with a second color highlighting 712 (e.g. red, yellow, black, or the like), and the color palette 704 may include a corresponding description 714 of the color highlighting 712. In various embodiments, another color or shading may be used to indicate a range of values that may or may not be voltage compliant, or promote intrinsic conduction. A variety of factors can influence measured impedance. For example, impedance may vary based on position of a patient (electrodes may shift during activity or when reclined), due to changes in proximity of electrode to target during pulse pressure wave of the cardiac cycle, or due to variability from measurements. The color highlighting 708 and the color highlighting 712 may be used to the user to identify which current amplitude values can be selected within the voltage compliance range of the IMD 102. The controller 302 may display many windows, either as an alternative to or in addition to the window 702 and color palette 704 to allow the user to select one or more neurostimulation parameters, such as current amplitude. For example, instead of the color highlighting 708 and 712 and the color palette 704, an alert pop-up window may appear on the display 306 when the user selects current amplitude for which the IMD 102 is not voltage compliant. The alert pop-up can have a help button for displaying additional information. The additional information can include current impedance measurement as a list, a trend, or on a plot of amplitude vs. impedance. In some embodiments, the programmer 104 can lockout buttons 706 representing current amplitudes for which the IMD 102 is not voltage compliant.

Various implantable systems use a passive recharge to maintain charge balance. The amount of recharge is dependent on the blocking capacitance, the impedance load and the time duration of the recharge, in various embodiments. Therefore, the maximum allowable programmed frequency of pulse delivery may be limited by the impedance load. The recharge period cannot be longer than the interval between pulses, and the recharge period needs to be longer at larger impedance loads than smaller impedance loads in order to maintain the same percentage of charge balance, in various embodiments. The amount of charge delivered in the active phase ($Q_1$) is current (I) times duration of the pulse width ($t_{pw}$), in an embodiment. The amount of charge passively recharged ($Q_2$) is $Q_1*(1-e^{-t/RC})$, where t is the duration of the recharge period, R is the impedance load, and C is the value of the blocking capacitor. Therefore, the amount of charge left after the first pulse is $Q_1-Q_2$. The system should reach steady state after multiple pulses are delivered, in various embodiments. The percentage of ($Q_1$) after recharge is $(Q_1-Q_2)/(Q_1)=e^{-t/RC}$ Maintaining charge balance is important for safety reasons (unbalanced charge can lead to nerve damage or lead dissolution) and for efficacy reasons (need higher output to capture as steady state voltage builds up on the blocking capacitor). Also, there may be a need to increase the power supply to the stimulation circuit in order to overcome the additional overhead of the steady state voltage, and increasing the power supply will have a negative effect on device longevity, in various embodiments. According to various embodiments, a message provided to a user using the display may inform the user regarding one or more of limitations on voltage compliance, charge density/nerve damage, longevity and frequency/recharge period. The message may be provided to the user using keys, legends or pop-ups on the display, in various embodiments (410 in FIG. 4 and also FIG. 7B).

In various embodiments, the blocking capacitor voltage increases during the current stimulation pulse and then partially discharges during the recharge time. As the blocking capacitor does not fully discharge in an embodiment, at the start of a stimulation burst, it "equilibrates" on a charge/discharge voltage average that is above 0 volts depending on the current amplitude, pulse width, impedance, and recharge time. The blocking capacitor voltage can be estimated by measuring the voltage across the load at the start and end of the recharge times, or it can be calculated.

In some instances, setting values of parameters (such as current amplitude, pulse width, or the like) too high may damage the patient's tissue or the stimulation electrodes 204. Thus, safety limits may be implemented, where the safety limits identify the highest value for the parameter (or highest value for the parameter (e.g. amplitude) with values for other parameters (e.g. pulse width or duty cycle of intermittent ON stimulation in which a train of pulse is delivered/OFF stimulation) that is considered safe. If values of the parameters that are selected by the user provide a charge density at the nervous tissue that is higher than a safe limit, the nervous tissue can be damaged. In addition, a charge density higher than the safety limit could lead to disintegration of lead electrodes 204 in the patient's body, which could further cause adverse reactions in the patient's body. By way of example, the safe limit of charge density for preventing nerve damage may range from 30 $\mu C/cm^2$ to 40 $\mu C/cm^2$, and the safe limit of charge density for platinum electrodes may range from 40 $\mu C/cm^2$ to 60 $\mu C/cm^2$. In various embodiments, the safe limit may be a cumulative charge or an average charge density.

The present subject matter includes an example of a method for determining the charge density at the electrodes 204 based on selection of certain neurostimulation (or other type of implanted therapy stimulation) parameters, such as, current amplitude, pulse width, or the like and communicating the average charge density to the user is described. In the method, the neurostimulation system 100 may be configured to sense tissue impedance and determine the range of values of parameters selected by the user that can safely deliver neurostimulation to the patient without increasing the charge density at the electrodes 204 above a safe limit. As described, the IMD 102 may sense the patient's tissue impedance and may determine voltage compliance of the IMD 102. If the IMD 102 is voltage compliant, the neurostimulation system 100 may determine charge density at the electrodes 204 as the current through the stimulation is known as well as the surface area of the electrode(s). The charge density of the electrodes 204 is the ratio of the total charge delivered over time using the electrodes 204 and the surface area of the electrodes 204. The surface of the electrodes may be determined for the electrode configuration. Current is charge per unit time, and thus charge can be determined by multiplying a constant current by the time the current is delivered. As the stimulation is delivered pulses, the charge delivered to the tissue using the electrodes over time is the product of the current amplitude for the pulse and pulse width parameter values selected by the user. Voltage compliance is measured prior to calculating the charge density because the current flowing through the IMD 102 changes from the current amplitude values selected by the user if the IMD 102 is not voltage compliant.

The surface area of the electrode 204 may be measured by a number of methods. In some embodiments, the user may manually input the lead model that is used in the neurostimulation system 100. For example, the user may select a number of preprogrammed lead models in a window on the display 306 using the I/O unit 308. Each lead model may have a different surface area for electrodes 204. Each lead may be able to use more than one electrode configuration for delivering the stimulation. In various embodiments, a nominal tolerance and a transition zone between safe and unsafe levels include an indication of nominal tolerance. The surface area for each of these potential electrode configurations may be determined. The programmer 104 may determine the surface area of the electrodes 204 depending upon the lead model selected by the user. In some other embodiments, the user can enter the serial number of the lead 202, and the programmer 104 can identify the specific surface area of the electrode(s) from the manufacturer specification associated with the lead serial number. If the lead has more than one electrode configuration that may be used to stimulate the neural tissue, the programmer 104 may also identify the specific surface area from the selected electrode configuration for the stimulation. In some embodiments, the user can directly input the value of the surface area of the electrodes 204 as an input parameter in the I/O unit 308.

After determining the total charge and the surface area of the electrodes 204, the programmer 104 may calculate the average charge density of the electrodes 204 by taking the ratio of the total charge calculated and the surface area of electrodes 204.

The safe limit of charge density for preventing nerve damage may be estimated or refined by taking feedback from the patient on tolerability of the therapy. For example, the neurostimulation procedure may be painful and uncomfortable for the patient when the charge density is higher than the safe limit. The user may input the safe limit for charge density in programmer 104 using the I/O unit 308 by testing the tolerance of the patient.

An example of a method for identifying a safe limit of charge density for preventing nerve damage may use a laryngeal vibration threshold. When the cervical vagus nerve is stimulated, laryngeal vibrations may be detected and used as an indicator of vagal nerve capture. If nerves get damaged, the laryngeal vibration threshold may change. In some embodiments, the IMD 102 includes one or more sensor(s) 208 to detect laryngeal vibrations (e.g. accelerometer, electromyogram (EMG) sensors, and acoustic sensors). The controller circuitry 212 may measure the threshold stimulation parameters that trigger laryngeal vibrations intermittently, and may communicate the threshold stimulation parameters to the programmer 104 using the telemetry circuitry 214. The telemetry unit 310 in the programmer 104 may receive and store the measured threshold stimulation parameters communicated by the IMD 102 in the memory 304. The controller 302 may calculate the safe limit of the charge density using the measured threshold parameters. The safe limit for preventing electrode disintegration is a theoretical limit and can be input by the user into the programmer 104 as a parameter using the I/O unit 308. The laryngeal vibration sensors may also be external sensors used in conjunction with the programmer within a clinical setting.

The controller 302 may compare the average charge density at the electrodes 204 with the safe limit of charge density to determine the potential for nerve damage. In addition to charge density and safe limit for charge density, the potential for nerve damage is affected by other parameters such as % duty cycle of the neurostimulation pulses, % timed to cardiac cycle plus heart rate, and individual lead characteristics. Further, the potential for lead dissolution depends upon the individual lead characteristics. In some embodiments, the IMD 102 has sensors to measure the above described parameters and determine the potential for nerve damage or lead dissolution. The controller 302 communicates the potential for nerve damage to the user by a visual stimulus, an audio tone/message, a vibration alert or the like or combinations thereof.

Figure 7B:
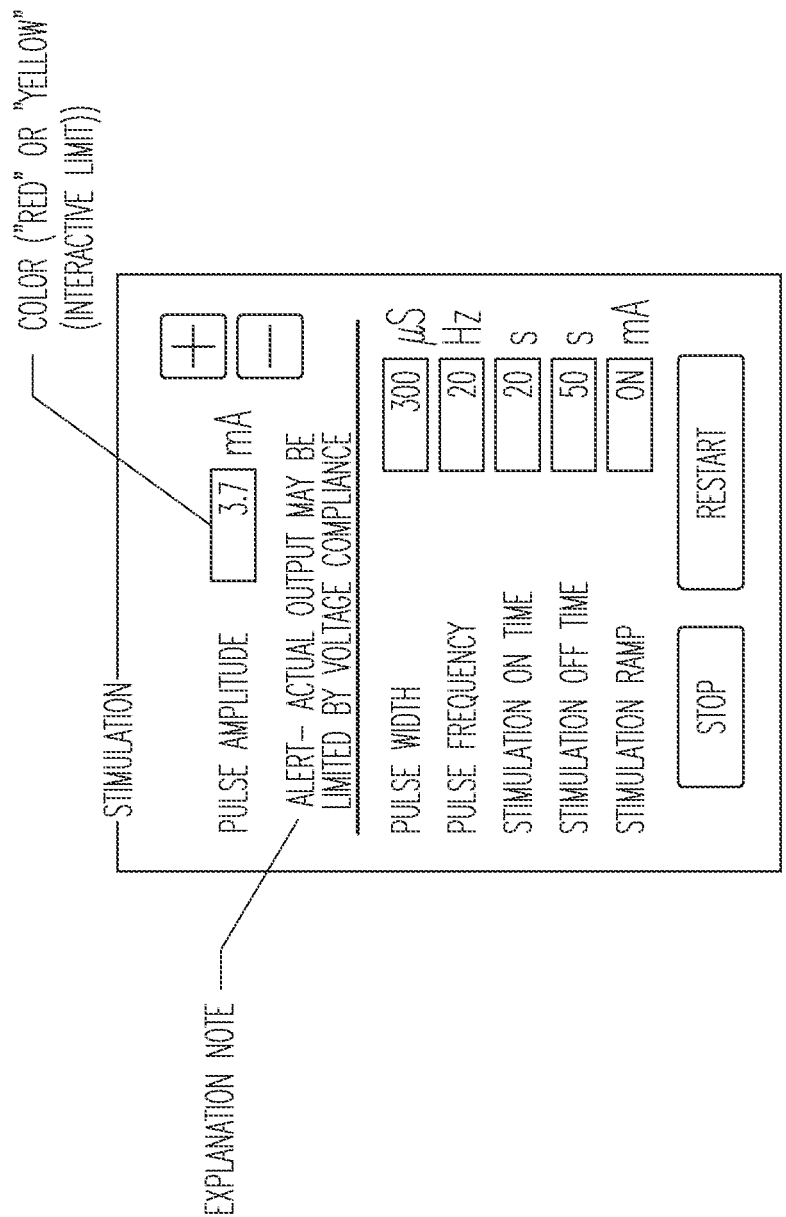
FIG. 7B illustrates an example of a parameter selection window, such as may be used to program the IMD of FIG. 1.
Figure 8:
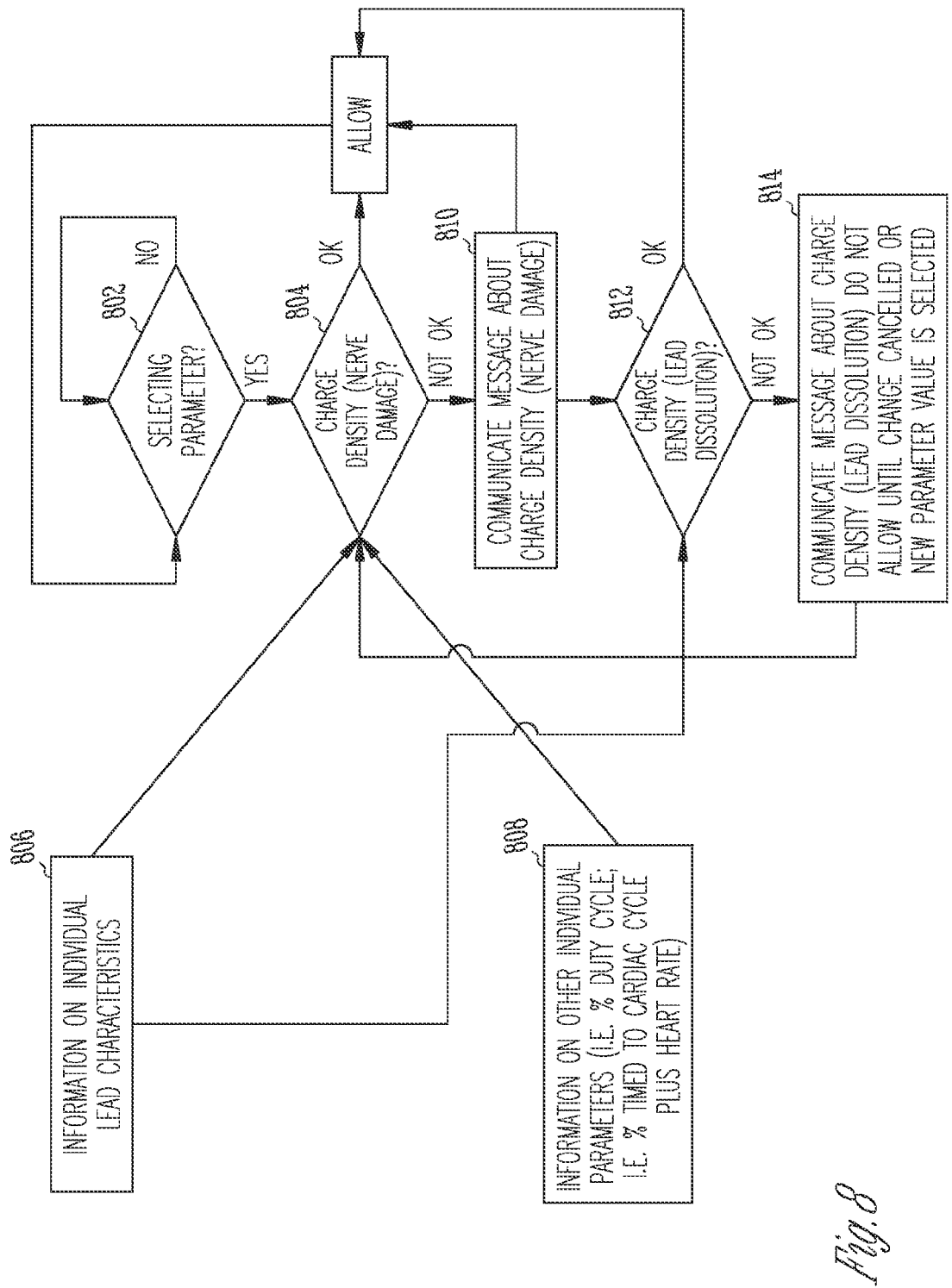
FIG. 8 illustrates an example of a method for communicating information related to the charge density at an electrode in communication with the IMD of FIG. 2.

In some embodiments, the controller 302 may provide a visual representation of the potential for nerve damage on the display 306. The user may make an informed decision about the limitations of selecting values of neurostimulation parameters, such as current amplitude, and pulse width using the displayed information. The controller 302 may display the potential for nerve damage by a number of methods. In various embodiments, the controller 302 creates a safety caution zone of parameter values that have a potential for nerve damage. The controller 302 may display an alert on the display 306, if the user selects the values of parameters that are in the safety caution zone. The controller 302 may display a warning or disallow selection of parameter values, if the user selects parameter values that indicate lead dissolution. In some embodiments, the controller 302 may display a color palette indicating the values of parameters that have potential for nerve damage or lead dissolution. FIG. 7B illustrates an example of a parameter selection window, such as may be used to program the IMD of FIG. 1;

FIG. 8 illustrates are example of a method for communicating the charge density at an electrode in communication with the IMD 102 of FIG. 2. The method may communicate the potential for nerve damage or lead dissolution, while a user selects one or more neurostimulation parameters. At 802, the programmer 104 may check if the user selects one or more neurostimulation parameters (e.g. the current amplitude, pulse width). The programmer 104 waits for the user to select a neurostimulation parameter. At 804, the programmer 104 checks if the charge density at electrodes 204 is within safe limits for nerve damage. At 806 and 808, additional parameters may be measured that may be used to monitor for potential nerve damage. At 804, the programmer 104 may determine potential for nerve damage based on the characteristics of individual leads 202. At 806, the programmer 104 may determine potential for nerve damage based on % duty cycle of the neurostimulation pulses or % timed to cardiac cycle plus heart rate. If the charge density is within safe limits and the other characteristics do not lead to potential nerve damage, then the programmer 104 may allow programming of the parameter values selected by the user.

At 810, if there is a potential for nerve damage by the IMD 102, then the programmer 104 may communicate a message about the potential for nerve damage by the IMD 102 to the user. The programmer 104 may communicate the message using a window on the display 306, in an embodiment.

At 812, the programmer 104 checks if the charge density at electrodes 204 is within safe limits for lead dissolution. The individual lead characteristics measured at 808 may be used to determine the potential for lead dissolution. If the charge density is within safe limits and the other characteristics do not lead to potential nerve damage, then the programmer 104 may allow programming of the parameter values selected by the user.

At 814, if there is a potential for lead dissolution, then the programmer 104 may communicate a message about the potential for lead dissolution to the user. The programmer 104 may communicate the message using a window on the display 306.

Figure 9A:
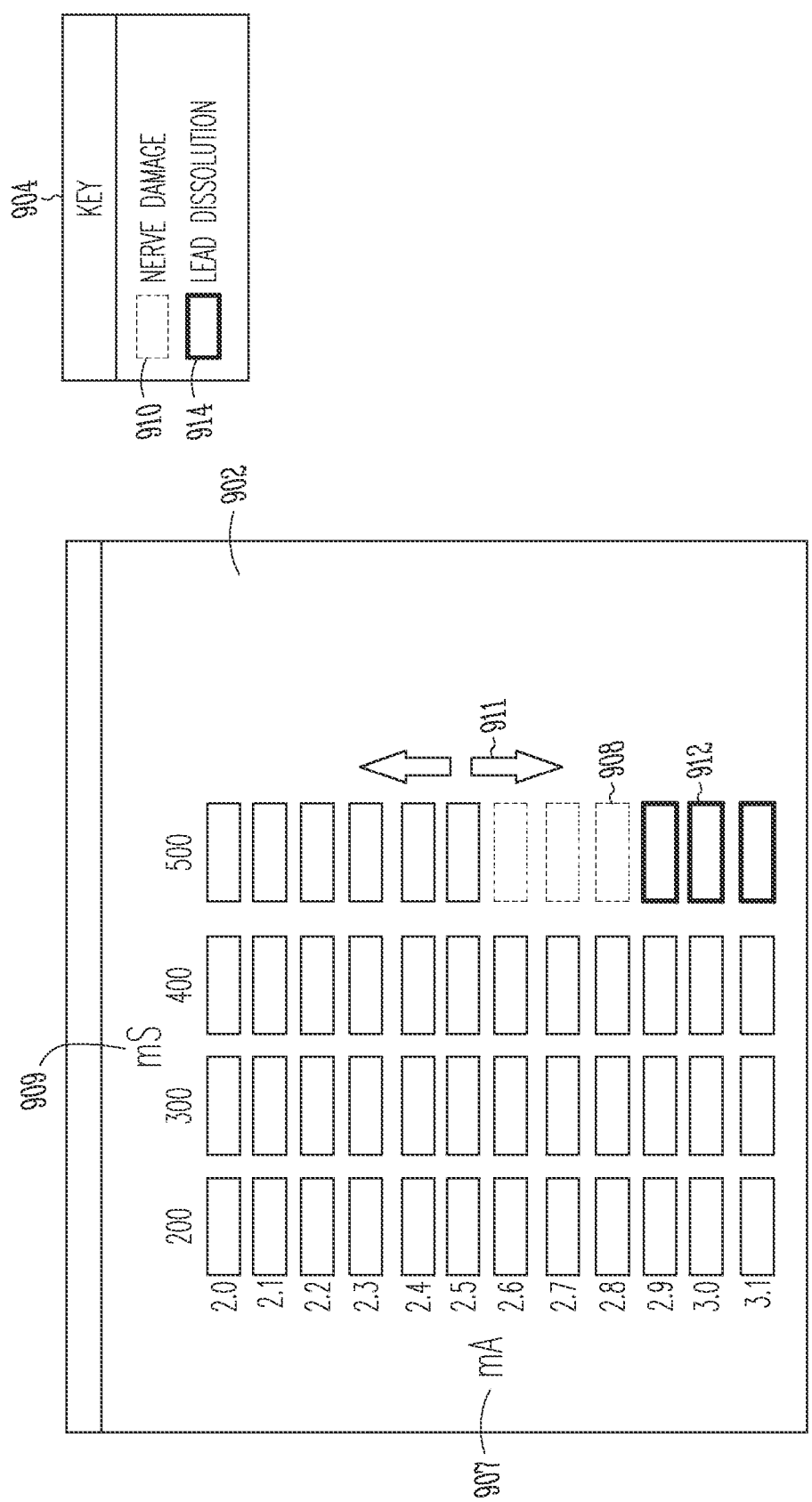
FIG. 9A illustrates an example of a charge density window and an associated color palette such as may be displayed on the programmer of FIG. 3.
Figures 9B, 9C:
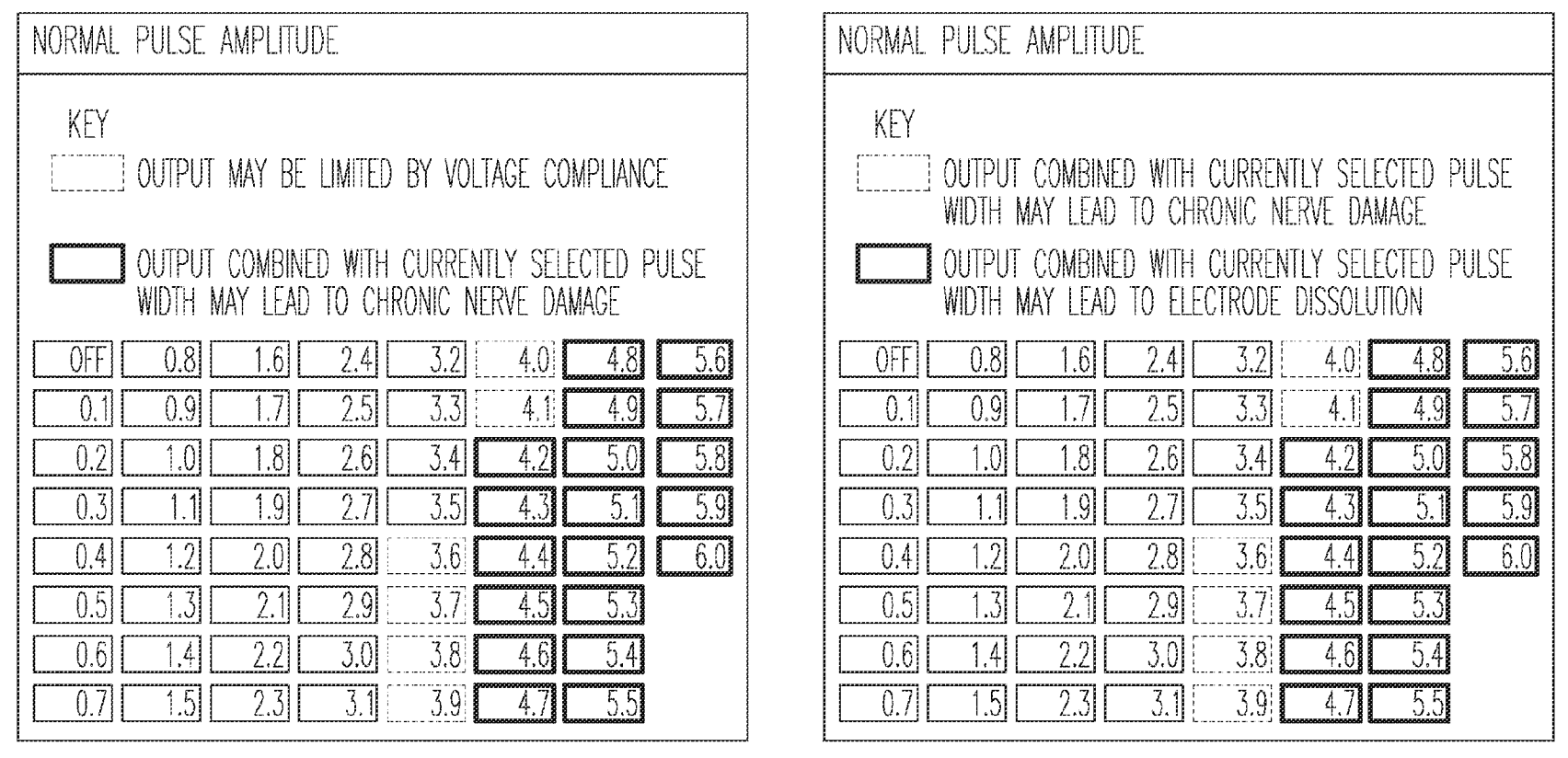

FIG. 9A illustrates an example of a charge density window 902 and an associated color palette 904 such as may be displayed on the programmer 104 of FIG. 3. The charge density window 902 allows a user to select one or more neurostimulation parameters (e.g. the current amplitude and pulse width of the neurostimulation pulses). The window 902 may include a number of buttons 906 in a matrix for selecting a combination of current amplitude on one axis 907 and pulse width on another axis 909 for neurostimulation. The buttons 906 may be accessed using one or more input devices in the I/O unit 308, for example, a touch screen or a pointing device such as a mouse, or the like. The programmer 104 may highlight the buttons 906 for which the IMD 102 has a potential for nerve damage with a first color highlighting 908 (e.g. green, blue, grey, or the like). The color palette 904 may include a corresponding description 910 of the color highlighting 908. The programmer 104 may highlight the buttons 906 for which the IMD 102 IMD 102 has a potential for lead dissolution with a second color highlighting 912 (e.g. red, yellow, black, or the like), and the color palette 904 may include a corresponding description 914 of the color highlighting 912. The color highlighting 908 and the color highlighting 912 may be used to communicate to the user which current amplitude and pulse width combinations can be selected to prevent nerve damage or lead dissolution by the IMD 102. In addition, the user may select a suitable combination of the current amplitude and pulse width using a pair of up and down arrows 911. The controller 302 may use many windows, either alternative to or in addition to the window 902 and color palette 904, to allow the user to select two or more neurostimulation parameter combinations, such as current amplitude and pulse width. For example, instead of the color highlighting 908 and 912 and the color palette 904, an alert pop-up window may appear on the display 306 when the user selects current amplitude and pulse width pair for which there is a potential for nerve damage or lead dissolution. The alert pop-up may have a help button for displaying additional information. The additional information may include a table of current amplitudes and corresponding pulse widths, a trend, or on a plot of amplitude vs. pulse width. In some embodiments, the programmer 104 may display lockout buttons 906 representing current amplitude and pulse width pairs for which there is a potential for nerve damage or lead dissolution.

In some instances, the parameters selected by the user may affect the longevity or battery life of the IMD 102. Certain parameter settings may drain the battery life or longevity of the battery in a short period of time. For example, some programming combinations can reduce the battery life of the IMD 102 by 2-3 years, and can act as a device longevity limitation for parameter selection.

Some embodiments may communicate the device longevity of the IMD 102 to the user. In an example, the neurostimulation system 100 may be configured to sense tissue impedance, determine the charge used over time, measure battery capacity, calculate longevity of IMD 102, and communicate longevity of IMD 102 to the user.

The IMD 102 may sense the patient's tissue impedance and determine voltage compliance of the IMD 102. If the IMD 102 is voltage compliant, the neurostimulation system 100 may calculate longevity of MID 102. Voltage compliance is measured prior to calculating the IMD 102 longevity because the current flowing through the MID 102 changes from the current amplitude value selected by the user if IMD 102 is not voltage compliant. The change in current amplitude value affects the calculation of longevity of IMD 102.

In some embodiments, the controller circuitry 212 in the IMD 102 may keep a log of the time for which the device was active, the current amplitude, pulse width, duty cycle, and frequency of the neurostimulation delivered and may use this information to calculate the charge used over time. In addition, the controller circuitry 212 may measure the battery capacity left in the MID 102. The controller circuitry 212 may communicate the calculated charge used over time and measured battery capacity to the programmer 104 using the telemetry link 106.

The programmer 104 may receive and store the sensed impedance, calculated charge used over time, and measured battery capacity communicated by the IMD 102 in the memory 304. The controller 302 may calculate the amount of charge required by the parameter value settings input by the user in the I/O unit 308. The controller 302 may calculate the device longevity for the IMD 102 based on the determined charge density, battery capacity, and the charge required by the parameters selected by the user. The controller 302 may communicate the device longevity to the user by a visual stimulus, an audio tone/message, a vibration alert or the like or combinations thereof.

In some embodiments, the controller 302 may display a visual representation of the device longevity on the display 306. The user can mike an informed decision about the device longevity limitation of the IMD 102, white selecting neurostimulation parameters, such as current amplitude, pulse width, duty cycle, pulse frequency or the like using the displayed device longevity.

The controller 302 can display the device longevity using a number of methods. For example the controller 302 may display a plot of device longevity in a window on the display 306. If the user selects values for a certain set of parameters, the controller 302 may display the estimated device longevity for those parameters in a plot having the parameter values on one axis and battery life of the IMD 102 on the other axis on the display 306. In some embodiments, the controller 302 may display a slider bar illustrating the device longevity along with a parameter selection window on the display 306. In some embodiments, the controller 302 may display a grey-scale plot of current amplitude versus pulse width indicating device longevity for the different values of these parameters on the display 306. In some embodiments, the controller 302 may display an interactive longevity display including a projected estimate on the display 306. FIGS.

9B-9C illustrate examples of a color palette display such as may be displayed on the programmer of FIG. 3.

Figure 10:
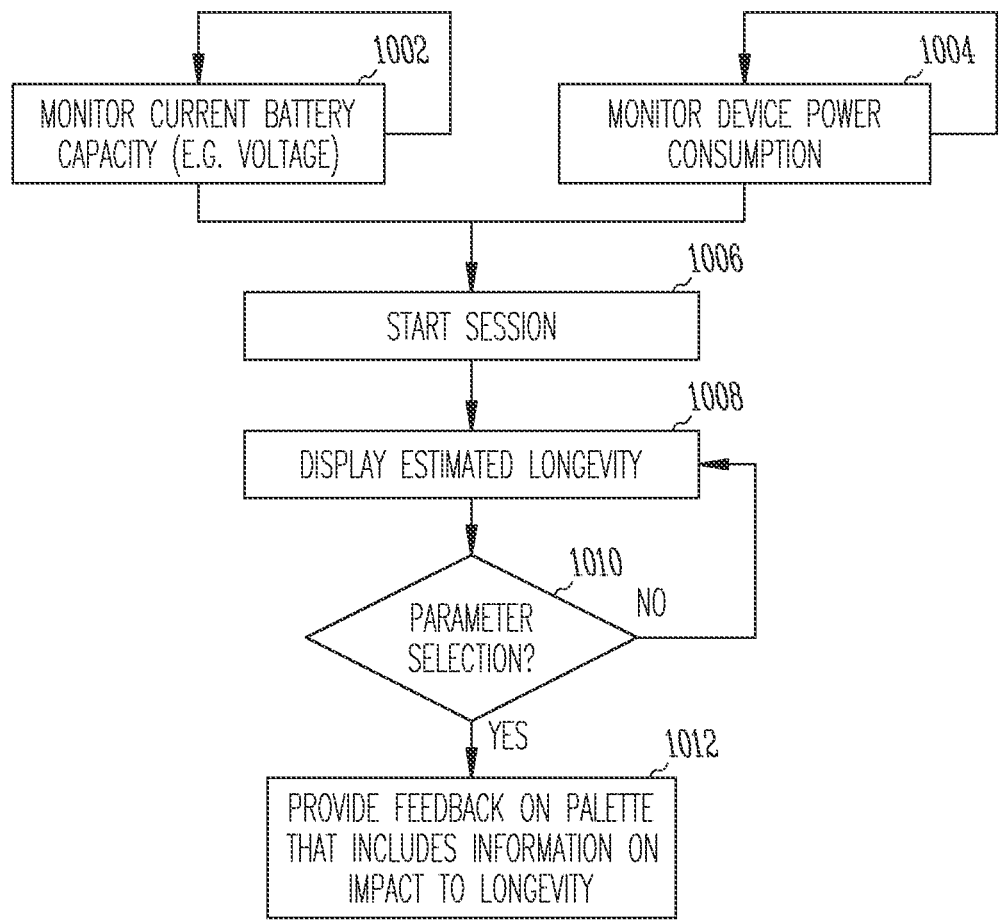
FIG. 10 illustrates an example of a method for communicating longevity and predicted longevity of the IMD of FIG. 2 to a user.

FIG. 10 illustrates an example of a method for communicating longevity of the IMD 102 of FIG. 2 to a user. At 1002, the IMD 102 may monitor the current battery capacity of the IMD 102. At 1004, the IMD 102 may monitor the power consumption. This monitoring may be intermittent (e.g. periodic according to a schedule or responsive to triggering events). The IMD 102 may store the measured current battery capacity and power consumption in the memory 216 and may communicate the current battery capacity and power consumption to the programmer 104.

At 1006 a programming session may be started. For example, a user may switch on the programmer 104 to start a new programming session, and the programmer 104 may form, upon startup, the telemetry link 106 with the IMD 102 to communicate with the IMD 102 and receive the current battery capacity and power consumption measurements made by the IMD 102.

At 1008, after startup of the programmer 104, the programmer 104 may calculate and display the IMD 102 longevity on the display 306 based on the current battery capacity and power consumption measurements communicated by the IMD 102.

At 1010, the programmer 104 may check if the user selects a neurostimulation parameter, for example, the current amplitude. The programmer 104 may wait for the user to select a neurostimulation parameter and update the IMD 102 longevity periodically on the display 306.

At 1012, if the user selects a parameter, the programmer 104 may calculate the estimated device longevity based on the parameter selected and the current battery capacity and power consumption measurements communicated by the IMD 102. In addition, the programmer 104 may update the estimated device longevity on the display 306.

Figure 11:
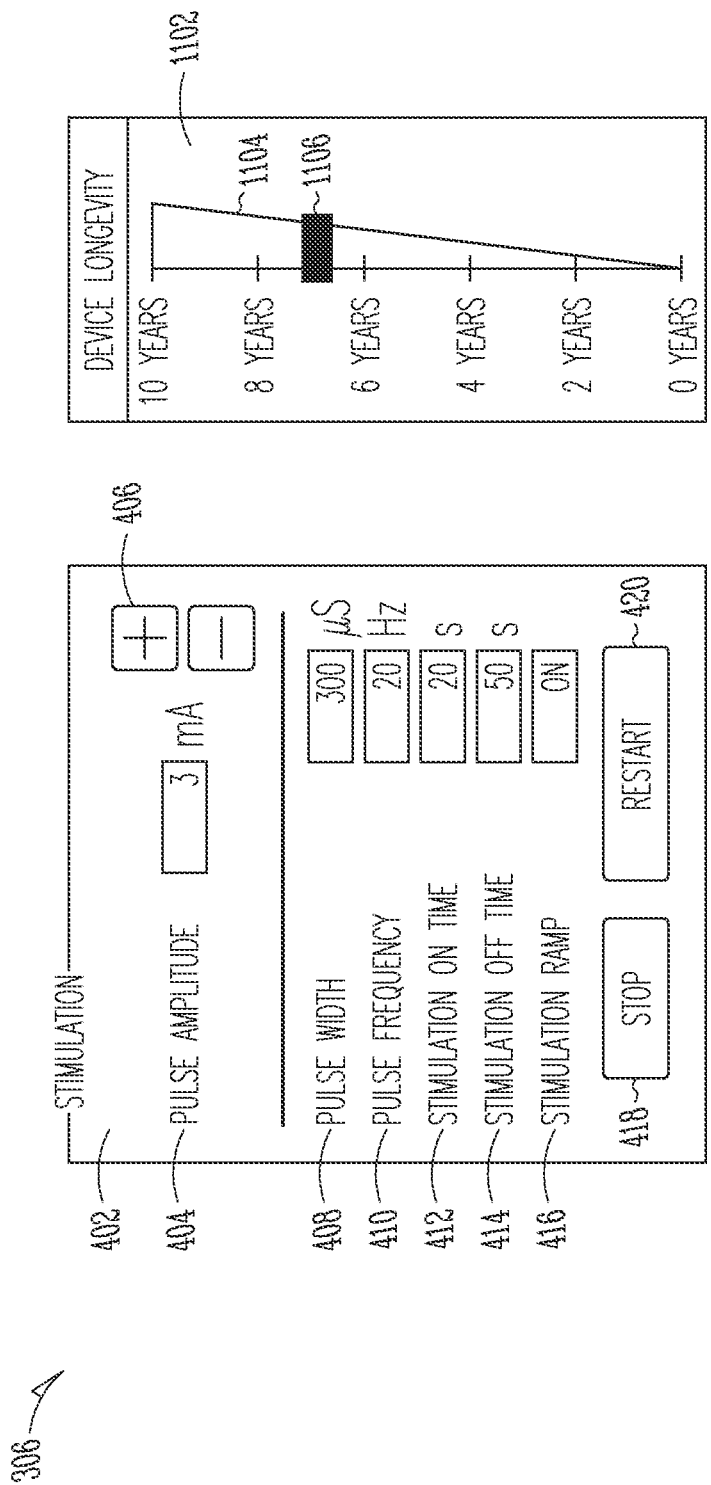
FIG. 11 illustrates the parameter selection window of FIG. 4 and an example of a device longevity window displayed on the programmer of FIG. 3.

FIG. 11 illustrates the parameter selection window 402 of FIG. 4 and an example of a device longevity window 1102 displayed on the programmer 104 of FIG. 3. The device longevity window 1102 allows a user to visualize the changes in device longevity when the user selects one or more neurostimulation parameters. The window 1102 may include a slider bar 1104 and a tab 1106, and the slider bar 1104 may include markings for device longevity ranging from 0 years to the maximum life span of the battery. In some instances, as shown, the maximum life span of the battery can be 10 years. When the user selects values of one or more neurostimulation parameters in the fields (e.g. pulse amplitude field 404) the programmer 104 may calculate the device longevity and moves the tab 1106 accordingly up or down on the slider bar 1104. The motion of the tab 1106 over the slider bar 1104 displays the estimated longevity of the IMD 102 to the user. The window 1102 is one of many windows that the controller 302 can show on the display 306 to allow the user to visualize device longevity. For example, instead of the window 1102, the programmer 104 can display longevity of IMD 102 as a grey-scale plot of amplitude vs. pulse width or amplitude vs. frequency.

As identified earlier, some MD embodiments may deliver a neurostimulation therapy, some IMD embodiments may deliver a cardiac rhythm management therapy, and some IMD embodiments may deliver both a neurostimulation therapy and a cardiac rhythm therapy. By way of example and not limitation, both neurostimulation and cardiac rhythm management therapies have been proposed to treat heart failure. For example, vagal stimulation therapy (VST) has been proposed to treat heart failure, and cardiac resynchronization therapy (CRT) and has been proposed to treat heart failure. However, vagal nerve stimulation can slow an intrinsic heart rate and/or increase the atrioventricular (AV) delay.

In some instances, the parameter values set by the physician could lead to right ventricle (RV) only pacing to compensate for the VST-induced slower heart rate or the VST-induced longer AV delays. However, RV only pacing, according to many clinical studies, may contribute toward heart failure. The parameter values that can lead to RV only pacing act as limitations for parameter selection by the user.

Some embodiments communicate the combination of parameter values that can lead to RV-only pacing and heart failure to the user is described. The neurostimulation system 100 may be configured to sense a parameter related to intrinsic AV delay heart rate for patient, determine a combination of parameters that will lead to increased RV only pacing, and communicate combination of parameters to the user. The Imp 102 may have one or more sensor(s) 208 to sense heart rate and parameters related to AV delay of the patient. The controller circuitry 212 may sense and communicate the heart rate and parameters related to AV delay to the programmer 104 using the telemetry link 106.

The programmer 104 may receive and store the sensed heart rate and parameters related to AV delay communicated by the MID 102 in the memory 304. The controller 302 may determine the values of input parameters that would lead to increased RV-only pacing for the patient based in part on the sensed parameters. In some embodiments, the controller 302 may characterize the intrinsic delay over a range of heart rates. In some embodiments, the controller 302 may determine the extent of AV block in the patient. The controller 302 may communicate the combination of input parameter values that will lead to RV-only pacing to prevent heart failure for the patient by a visual stimulus, an audio tone/message, a vibration alert or the like or combinations thereof.

In some embodiments, the controller 302 provide a visual representation of the combination of input parameter values that will lead to RV-only pacing on the display 306 to communicate with the user. The user can make an informed decision about the risk of heart failure due to neurostimulation by the IMD 102, while selecting neurostimulation parameters, such as current amplitude, pulse width, pulse frequency or the like using the displayed combination of input parameter values that increases the likelihood of triggering RV-only pacing.

The controller 302 may display the combination of input parameter values that increase the likelihood of triggering RV-only pacing by a number of methods. The controller 302 may provide real time information on a lower rate limit (LRL) of heart rate that will lead to increased RV only pacing on the display 306. The controller 302 may provide real-time information on AV delay that would lead to RV-only pacing on the display 306.

Figure 12:
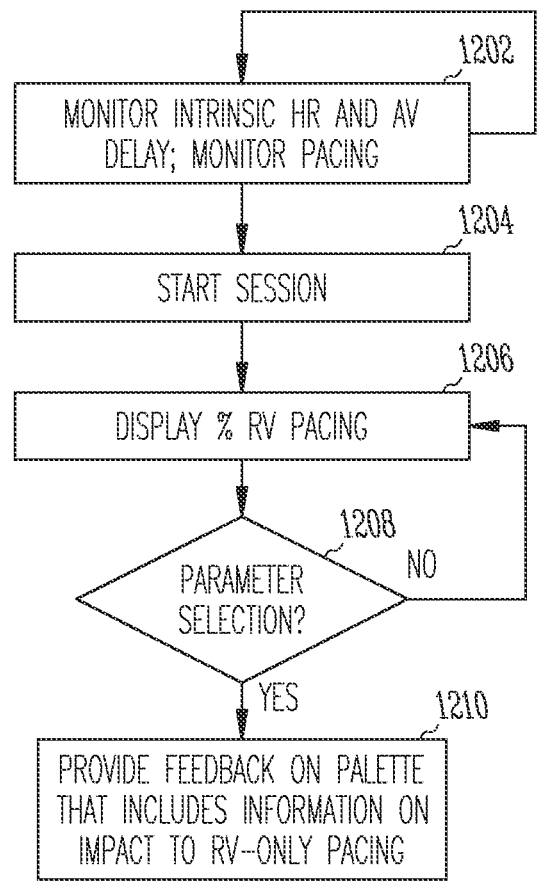
FIG. 12 illustrates an example of a method for communicating the risk of RV-only pacing.

FIG. 12 illustrates an example of a method tier communicating the risk of RV-only pacing. At 1202, the IMD 102 may monitor the current heart rate of the patient, intrinsic AV delay of the patient, and pacing of the HAD 102 periodically. The IMD 102 may store the periodically measured heart rate, AV delay, and pacing data in the memory 216 and may communicate the data to the programmer 104.

At 1204 a programming session may start. For example, a user may switch on the programmer 104 to start a new programming session. Upon startup, the programmer 104 may form the telemetry link 106 with the IMD 102 to communicate with the IMD 102 and receive the periodic heart rate, AV delay, and pacing measurements made by the IMD 102.

At 1208, after startup of the programmer 104, the programmer 104 may calculate and display the risk of RV-only pacing on the display 306 based on the periodic heart rate, AV delay, and pacing measurements communicated by the IMD 102.

At 1210, the programmer 104 may check if the user selects a CRM stimulation or neurostimulation parameter (e.g. the current amplitude). The programmer 104 may wait for the user to select a stimulation parameter and updates risk of RV-only pacing periodically on the display 306.

At 1212, if the user selects a parameter, the programmer 104 may determine the risk of RV-only pacing based on the parameter selected and the periodic heart rate, AV delay, and pacing measurements communicated by the IMD 102. The programmer 104 may update the risk of RV-only pacing on the display 306.

Figure 13A:
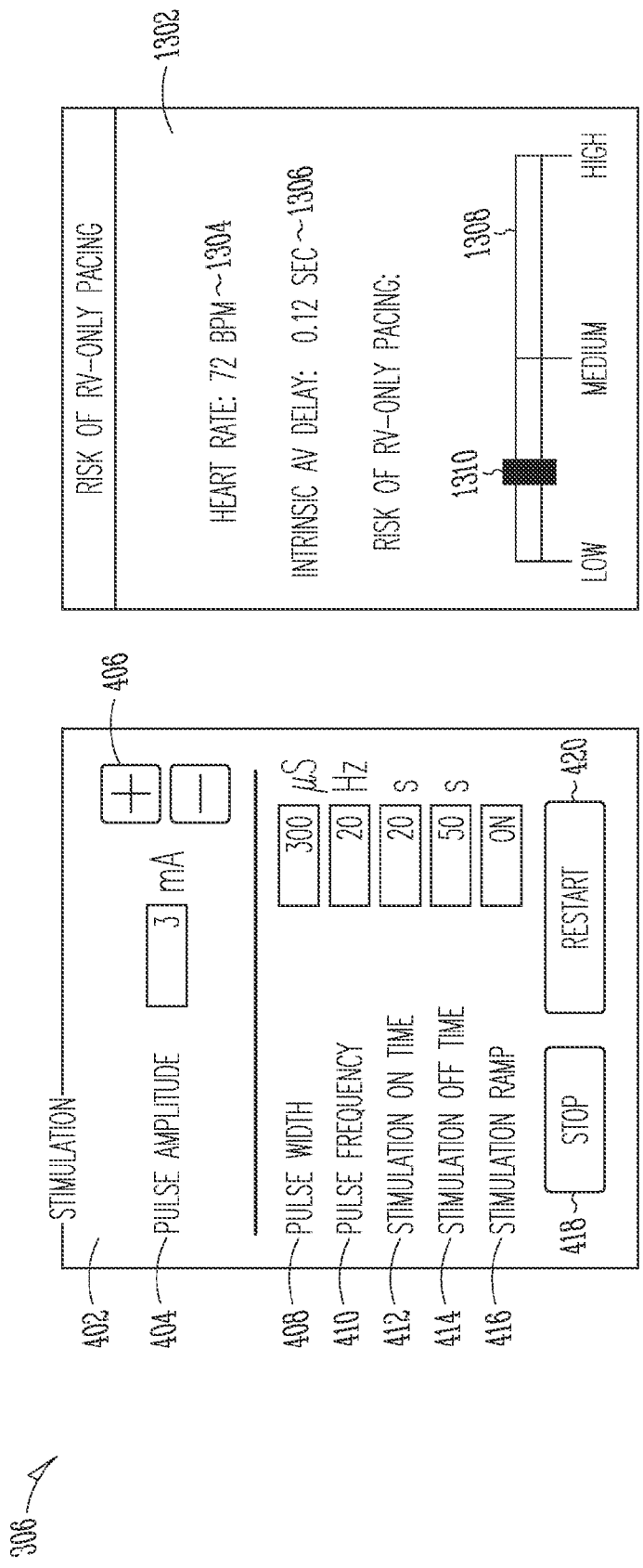
FIG. 13A illustrates the parameter selection window of FIG. 4 and an example of an RV-only pacing window displayed on the programmer of FIG. 3.
Figure 13B:
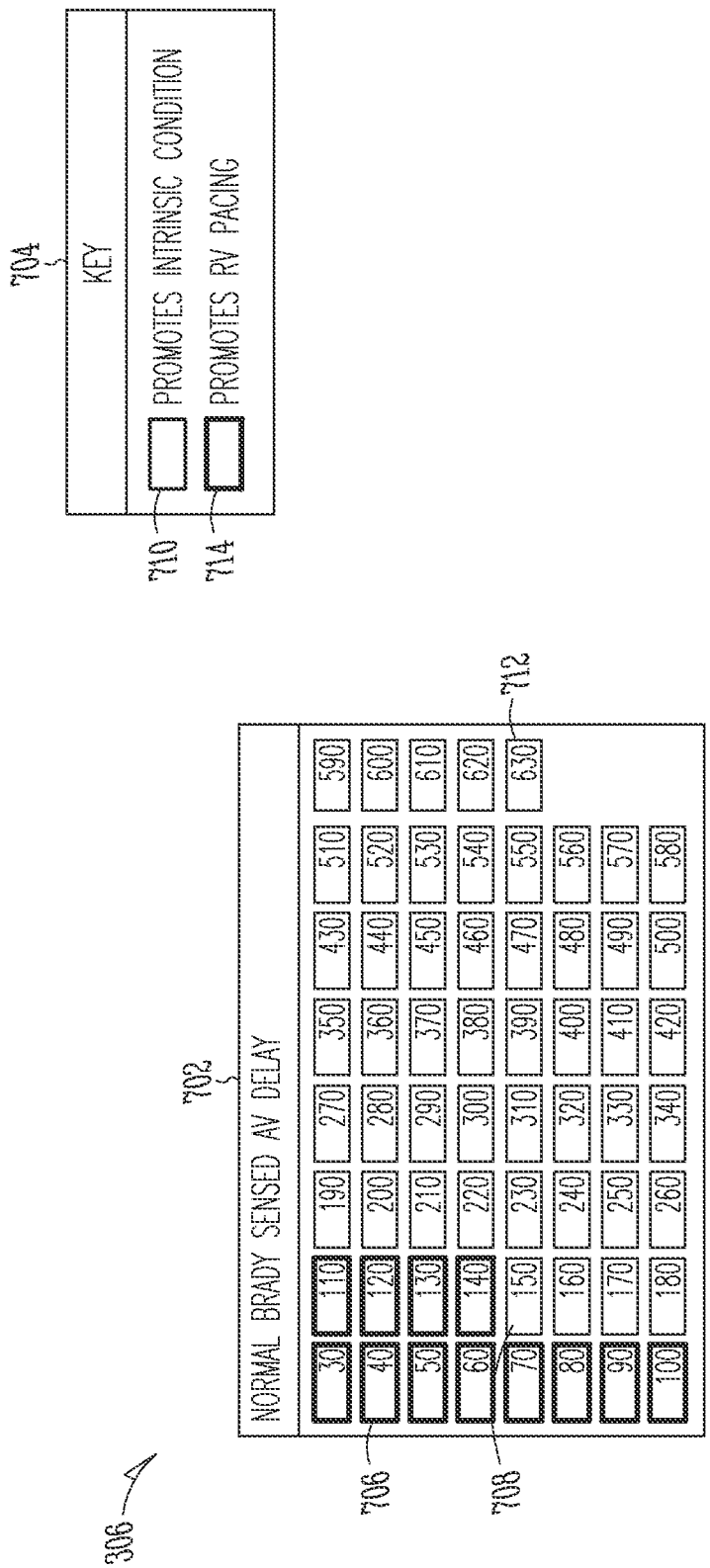
Figure 13C:
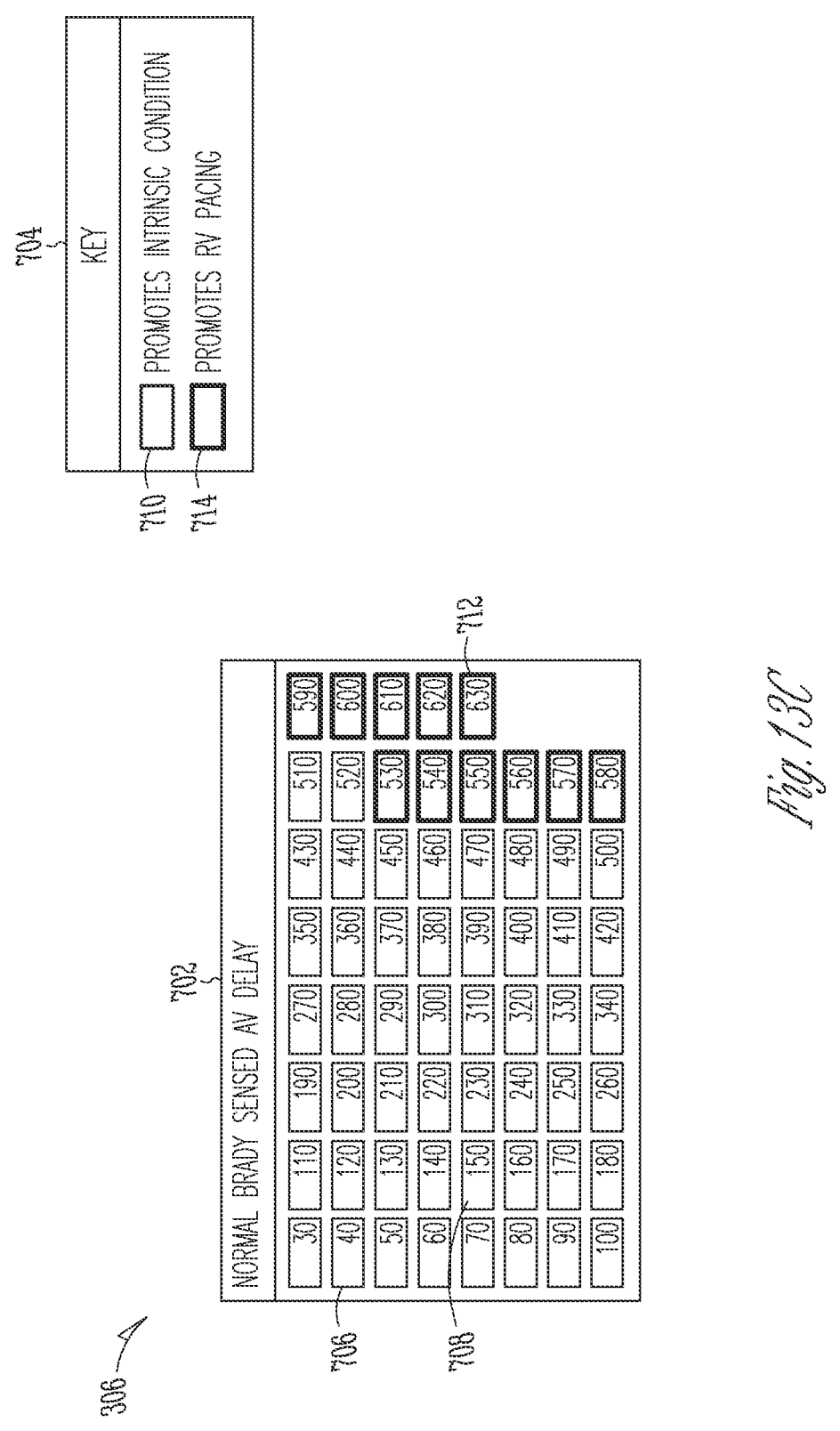

FIG. 13A illustrates the parameter selection window 402 of FIG. 4 and an example of an RV-only pacing window 1302 displayed on the programmer 104 of FIG. 3 to allow a user to visualize the risk of RV only pacing when the user select one or more neurostimulation parameters. The window 1302 may include a heart rate field 1304 indicating the real time heart rate of the patient, an intrinsic AV delay field 1306 indicating the intrinsic AV delay of the patient in real time, a slider bar 1308 and a tab 1310. The slider bar 1308 may include markings for risk of RV only pacing, for example, low, medium, high, or the like. When the user selects values in one or more neurostimulation parameter fields (e.g. pulse amplitude field 404), the programmer 104 may determine the risk of RV only pacing and move the tab 1310 accordingly right or left on the slider bar 1308. The motion of the tab 1310 over the slider bar 1308 displays the estimated longevity of the IMD 102 to the user. The window 1302 is one of many windows that the controller 302 can show on the display 306 to allow the user to visualize risk of RV-only pacing. FIGS. 13B-13C illustrate embodiments of an interactive window 1382 and a color palette 1384 for display on the programmer of FIG. 3 to allow a user to select a stimulation parameter to promote RV pacing.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   measuring a parameter according to a programmed schedule, the parameter associated with a biological environment, for a system including an implantable medical device (IMD) configured for delivering electrical stimulation therapy;
   determining an upper limit of the therapy that can be delivered by the IMD based on the measured parameter, including determining potentiality for nerve damage from therapy delivery by the IMD based on the parameter; and
   displaying the limit to a user using an interface of an external device, including displaying the potentiality for nerve damage from therapy delivery by the IMD, the external device configured to communicate with the IMD.

2. The method of claim 1, wherein measuring a parameter associated with biological environment includes sensing impedance for at least a portion of a lead system connected to the IMD.

3. The method of claim 2, wherein determining a limit of the therapy includes determining voltage compliance based on the sensed impedance and calculating a limit of electric current level that can be delivered by the IMD based on the determined voltage compliance.

4. The method of claim 3, further comprising using a color code to display the calculated limit.

5. The method of claim 3, wherein displaying the limit includes displaying a color palette with selections for programming parameters for delivering therapy.

6. The method of claim 2, further comprising:
   determining charge density based on the sensed impedance;
   determining potential for nerve damage from therapy delivery by the based on the determined charge density; and
   displaying the determined potential for nerve damage using the interface.

7. The method of claim 2, further comprising:
   determining maximum allowable programmed frequency of pulse delivery based on the sensed impedance load and time duration of recharge; and
   displaying the maximum allowable programmed frequency of pulse delivery to a user using the interface.

8. The method of claim 2; further comprising:
   determining charge used over time based on the sensed impedance and settings input by the user;
   measuring battery capacity for the IMD;
   calculating device longevity for the IMD based on the determined charge and battery capacity; and
   displaying the device longevity to a user using the interface.

9. The method of claim 8, wherein the displaying includes displaying an interactive longevity display including a projected estimate.

10. The method of claim 1, wherein delivering electrical stimulation therapy includes delivering neurostimulation therapy.

11. The method of claim 1, wherein delivering electrical stimulation therapy includes delivering cardiac rhythm management (CRM) therapy.

12. The method of claim 1, wherein measuring a parameter includes sensing a parameter related to intrinsic cardiac function for a patient.

13. The method of claim 12, further comprising:
   determining a combination of input parameters for a therapy that increase a likelihood of undesired amounts of cardiac pacing for the patient based in part on the sensed parameter; and
   displaying the combination of input parameters to a user using the interface.

14. The method of claim 13, wherein the displaying includes providing real-time information on a lower rate limit (LRL) that will lead to decreased RV-only pacing.

15. The method of claim 13, wherein the displaying includes providing real-time information on an AV delay that will lead to decreased RV-only pacing.

* * * * *